(12) United States Patent
Mandal et al.

(10) Patent No.: US 12,361,839 B2
(45) Date of Patent: Jul. 15, 2025

(54) SYSTEM AND METHOD FOR SIMULATION AND UNDERSTANDING EMBRYOLOGY

(71) Applicant: IMMERSIVEVISION TECHNOLOGY PVT. LTD, Pune (IN)

(72) Inventors: Navin Mandal, Thane (IN); Amit Ranjan, Pune (IN); Amresh Kumar, Mumbai (IN); Nitin Dongre, Pune (IN); Sneha Adsule, Pune (IN)

(73) Assignee: IMMERSIVEVISION TECHNOLOGY PVT. LTD (IN)

( * ) Notice: Subject to any disclaimer, the term of this patent is extended or adjusted under 35 U.S.C. 154(b) by 0 days.

(21) Appl. No.: 18/755,749

(22) Filed: Jun. 27, 2024

(65) Prior Publication Data

US 2025/0037596 A1    Jan. 30, 2025

(30) Foreign Application Priority Data

Jul. 27, 2023    (IN) .............................. 202321050722

(51) Int. Cl.
| | |
|---|---|
| *G09B 5/06* | (2006.01) |
| *A61B 34/10* | (2016.01) |
| *G06T 13/20* | (2011.01) |
| *G16B 5/00* | (2019.01) |

(52) U.S. Cl.
CPC .............. *G09B 5/065* (2013.01); *A61B 34/10* (2016.02); *G06T 13/20* (2013.01); *G16B 5/00* (2019.02); *A61B 2034/105* (2016.02); *G06T 2200/24* (2013.01); *G06T 2210/41* (2013.01)

(58) Field of Classification Search
CPC ... G09B 5/065; A61B 34/10; A61B 2034/105; G06T 13/20; G06T 2200/24; G06T 2210/41; G16B 5/00
See application file for complete search history.

(56) References Cited

U.S. PATENT DOCUMENTS

| | | | | |
|---|---|---|---|---|
| 5,621,671 | A * | 4/1997 | Bodnar | G16B 5/00 703/11 |
| 7,305,331 | B2 * | 12/2007 | Allen | G16B 5/00 703/11 |
| 10,282,513 | B2 * | 5/2019 | Brubaker | G16B 15/00 |
| 11,288,863 | B2 * | 3/2022 | Crowe | G06T 7/90 |
| 12,178,641 | B2 * | 12/2024 | Sun | A61B 8/5246 |

(Continued)

FOREIGN PATENT DOCUMENTS

| | | |
|---|---|---|
| CN | 104881292 A | 9/2015 |
| CN | 114550554 A | 5/2022 |

*Primary Examiner* — Jack Yip

(57) ABSTRACT

The system (100) and method for simulation and understanding embryology, as compared to prior-arts, is capable to help understand embryology by simulation. System (100) and method includes a processing system (10) that has an interactive module (20) which receives selection of a user from a general embryology module (20*a*), a systemic embryology module (20*b*), a genetics module (20*c*), and a stem cells module (20*d*). The system (100) and method also includes a text module (30) to display text, an audio-video module (40) to play a three-dimensional simulation module (50) to allow simulation, a fetal surgery and intervention simulation module (60) and a comparative module (70) to allow comparison of fetal anatomical structures and physiology at different developmental stages of age to adults.

6 Claims, 18 Drawing Sheets

(56) References Cited

U.S. PATENT DOCUMENTS

| | | | |
|---|---|---|---|
| 2002/0150941 A1* | 10/2002 | Gojobori | G06G 7/48 |
| | | | 703/11 |
| 2010/0305929 A1* | 12/2010 | Andersen | G16B 5/00 |
| | | | 703/11 |
| 2014/0067422 A1* | 3/2014 | Kim | G16H 30/20 |
| | | | 705/3 |
| 2016/0055292 A1* | 2/2016 | White | G06T 11/206 |
| | | | 702/19 |
| 2019/0026935 A1* | 1/2019 | Podziemski | G06F 3/017 |
| 2021/0315539 A1 | 10/2021 | Lee et al. | |
| 2024/0029253 A1* | 1/2024 | Tani | G06T 17/00 |
| 2024/0249142 A1* | 7/2024 | Erlich | G06N 3/09 |

\* cited by examiner

SYSTEM AND METHOD FOR SIMULATION AND UNDERSTANDING EMBRYOLOGY

FIELD OF THE INVENTION

The present disclosure relates to a learning platform. Particularly, the present disclosure relates to a simulation and understanding embryology system that facilitates a user to understand embryology.

BACKGROUND OF THE INVENTION

Embryology, the study of embryo development, plays a crucial role in understanding the formation and growth of organisms before birth. Embryology encompasses both the embryonic and fetal periods in humans, providing insights into the intricate processes that shape an individual's development. As scientific knowledge in the field of embryology continues to evolve, there is a growing need to update and enhance the teaching methods employed in medical education.

Traditionally, embryology has been taught through textbooks and lectures, relying on static diagrams and descriptive text to convey complex developmental processes. However, the current medical curriculum often falls short in incorporating the latest developments in the field of embryology. It tends to focus on anatomical details, neglecting important modern subjects such as Genetics, Stem cells, Genetic defects, Congenital defects, and clinical cases. To address this challenge, there is a need to develop a combined platform that encompasses both the basics of embryology and the latest advancements in the field. By integrating these subjects into the curriculum, students can gain a comprehensive understanding of embryology and its applications in modern medicine.

However, the current medical curriculum often falls short in incorporating the latest developments in the field of embryology. Presently, there is focus on anatomical details, neglecting the importance of genetics, stem cells, genetic defects, congenital defects, and clinical cases. To address this challenge, there is a need to develop a combined platform that encompasses both the basics of embryology and the latest advancements in the field. By integrating these subjects into the curriculum, students can gain a comprehensive understanding of embryology and its applications in modern medicine.

Furthermore, recent advancements in medical science have brought attention to fetal interventions, which involve medical treatments performed on a growing fetus before or shortly after birth to detect or cure medical issues. Fetal surgeries and interventions are complex procedures that have the potential to save the lives of both the fetus and the mother. However, explaining these procedures solely through text or traditional teaching methods can be challenging.

Thus, there is a need for a system and method for simulation and understanding embryology.

OBJECTS OF THE INVENTION

Some of the objects of the arrangement of the present disclosure are aimed to ameliorate one or more problems of the prior art or to at least provide a useful alternative and are listed herein below.

A principle object of the present disclosure is to provide a system and method for simulation and understanding embryology to enhance understanding, improve the experience, and contribute to the advancement of medical education in the field of embryology by way of interactive simulations, comprehensive coverage, comparative embryology, and fetal surgery and intervention simulations.

Another object of the present disclosure is to provide a system and method for simulation and understanding embryology by interactive simulations that utilize animations, 3D models, and a step-by-step guide for each embryonic developmental stage.

Still another object of the present disclosure is to provide a system and method for simulation and understanding embryology that includes understanding of genetics, stem cells and their applications, genetic defects, congenital defects, and clinical cases.

Yet another object of the present disclosure is to provide a method for explaining comparative embryology at different developmental stages using virtual three-dimensional models.

Another object of the present disclosure is to provide a system and method for simulation and understanding embryology that allows simulations to illustrate fetal surgeries, which are otherwise difficult to convey through text or traditional methods.

Other objects and advantages of the present disclosure will be more apparent from the following description when read in conjunction with the accompanying figures, which are not intended to limit the scope of the present disclosure.

SUMMARY OF THE INVENTION

The present invention discloses a simulation and understanding embryology system, in accordance with the one embodiment of the present invention. The present invention relates to a simulation and understanding embryology system that revolutionizes the understanding of embryology through an interactive and comprehensive approach. The system includes a processing system, an interactive module, a text module, an audio-video module and a three-dimensional simulation module. The processing system is hosted on a server and accessed through a device after registration. The processing system includes an interactive module that allows users to select from various modules, such as general embryology, systemic embryology, genetics and stem cells. Within the general embryology module, users can select a specific week module, which further provides options for selecting from a developmental-Carnegie stages module and a cellular-Carnegie stages module. Similarly, within the systemic embryology module, users can choose the skeletal system module, which offers a development module and a congenital disorder module. The development module allows selection from various sub-modules, including an introduction module, vertebral column development module, rib cage module, sternum module, skull module, formation of limbs module and joints module. The congenital disorder module provides options for studying anomalies of the vertebral column, sternum and ribs, skull and limbs. Furthermore, the interactive module includes a genetics module that allows users to access a basic genetic module, which provides selections for genes and chromosomes sub-modules. The genes module offers modules on DNA and RNA, control of embryo development and components required for gene expression. The chromosomes module provides options for studying haploid and diploid chromosomes. Additionally, a genetic disorder module allows users to explore chromosomal abnormalities, inheritance of genetic disorders, congenital defects, and clinical correlations. The chromosomal abnormalities module further includes sub-modules on Patau's syndrome and Turner syndrome, while the inheritance of genetic disorders module offers a pedigree chart module and an autosomal dominant inheritance module. Moreover, the interactive module incorporates a stem cells module that covers basic and clinical importance modules. The basic module allows selection of an introduction module, a stem cells production module, sources for stem cells module, and a classification module. The clinical importance module offers modules on therapeutic uses and examples. The simulation and understanding embryology system also includes the text module that displays text corresponding to the user's selection from the interactive module. Additionally, an audio-video module enables the playing of audio and video content related to the selected modules. Furthermore, a three-dimensional simulation module allows users to engage with interactive three-dimensional models associated with their chosen modules from the interactive module. In summary, the present invention provides a simulation and understanding embryology system that offers an innovative and comprehensive approach for understanding embryology. The system utilizes interactive modules to enable users to select specific modules, which are complemented by text, audio-video, and three-dimensional simulation modules. This system facilitates a more engaging and effective learning experience, enhancing students' understanding of embryology and its various aspects. Further, a fetal surgery and intervention simulation module is provided to perform fetal surgery through the three-dimensional simulation module (50). Furthermore, there is provided a comparative module to allow comparison of fetal anatomical structures and physiology at different developmental stages of age to adults. The interactive module, the text module (30), the audio-video module (40), the three-dimensional simulation module (50), the fetal surgery and intervention simulation module (60) and the comparative module are interlinked. In one embodiment, the simulation is performed by use of an oculus wearable on user's head and haptic sensors wearable in hands, wherein said oculus and haptic sensors are connected to the device. In one embodiment, the simulation is performed by operating the touch screen of said device.

The present disclosure also discloses a method for simulation and understanding embryology. The method includes utilizing a simulation and understanding embryology system which includes a processing system, an interactive module, a text module, an audio-video module, and a three-dimensional simulation module. The method involves the following steps:

1) User Selection: The user selects from the interactive module of the system. The interactive module offers various modules, including general embryology, systemic embryology, genetics, and stem cells.
2) General Embryology Selection: Within the general embryology module, the user can select a specific week module, which further allows selection from a developmental-Carnegie stages module and a cellular-Carnegie stages module.
3) Systemic Embryology Selection: In the systemic embryology module, the user can choose the skeletal system module, which provides options for selecting a development module and a congenital disorder module. The development module includes sub-modules such as introduction, vertebral column development, rib cage, sternum, skull, formation of limbs, and joints. The congenital disorder module offers selections for anomalies of the vertebral column, sternum and ribs, skull, and limbs.
4) Genetics Selection: Within the genetics module, the user can access the basic genetic module, which provides selections for genes and chromosomes sub-modules. The genes module includes sub-modules such as DNA and RNA, control of embryo development, and components required for gene expression. The chromosomes module offers options for studying haploid and diploid chromosomes. Additionally, the user can choose the genetic disorder module, which includes sub-modules on chromosomal abnormalities, inheritance of genetic disorders, congenital defects, and clinical correlations. The chromosomal abnormalities module provides options for studying Patau's syndrome and Turner syndrome, while the inheritance of genetic disorders module offers a pedigree chart module and an autosomal dominant inheritance module.
5) Stem Cells Selection: The user can select the stem cells module, which includes a basic module. The basic module allows selections for an introduction module and a clinical importance module. The introduction module offers further selections for a stem cells production module, sources for stem cells module, and a classification module. The clinical importance module provides options for studying therapeutic uses and examples of stem cells.
6) Text and Audio-Video Selection: The user selects the text module and the audio-video module through the device to display relevant text and play audio-video content based on the selections made in the interactive module.
7) Three-Dimensional Simulation: The user also selects the three-dimensional simulation module through the device, enabling the simulation of three-dimensional models associated with the selected modules from the interactive module. This allows the user to engage in interactive three-dimensional simulations related to embryology.
8) Perform Three-Dimensional Simulation: The user, through the device, performs three-dimensional simulation based on the selected modules and engages with the interactive three-dimensional models provided by the system.

In conclusion, the method for simulation and understanding embryology involves the selection of modules from the interactive module of the simulation and understanding embryology system. The user can access relevant text, audio-video content, and engage in three-dimensional simulations, enhancing the understanding and learning experience in the field of embryology.

In one embodiment, the step includes performing the simulation by use of an oculus wearable on user's head and haptic sensors wearable in hands, wherein the oculus and haptic sensors are connected to the device.

In one embodiment, the step includes performing simulation by operating the touch screen of the device.

BRIEF DESCRIPTION OF ACCOMPANYING DRAWINGS

The present disclosure will now be described with the help of the accompanying drawings, in which.

DETAILED DESCRIPTION OF THE INVENTION

Figure 1:
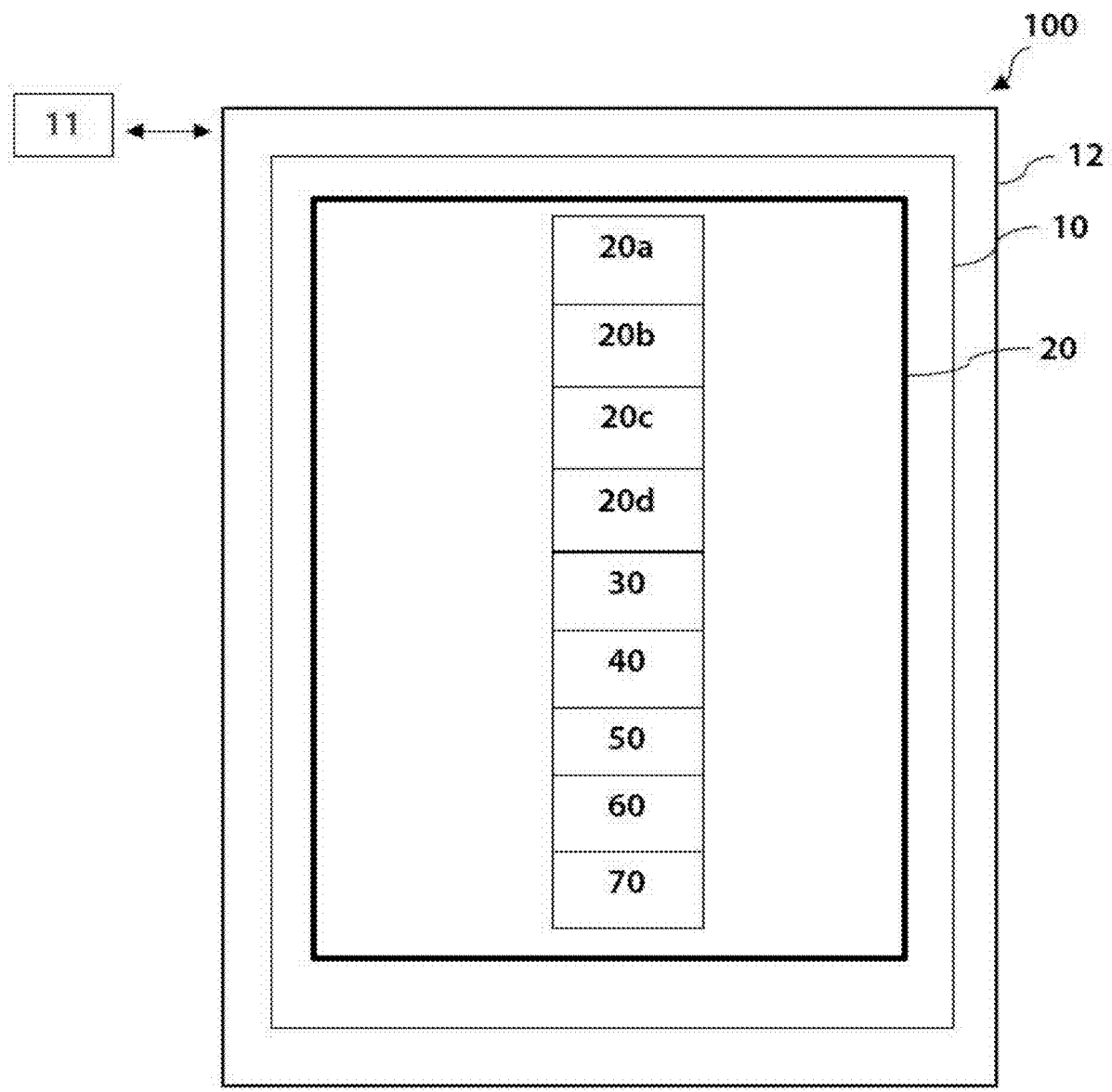
FIG. 1 illustrates a schematic representation of a system (100) for simulation and understanding embryology, in accordance with one embodiment of the present disclosure, which includes a processing system (10), an interactive module (20), a text module (30), an audio-video module (40) and a three-dimensional simulation module (50)
Figure 2:
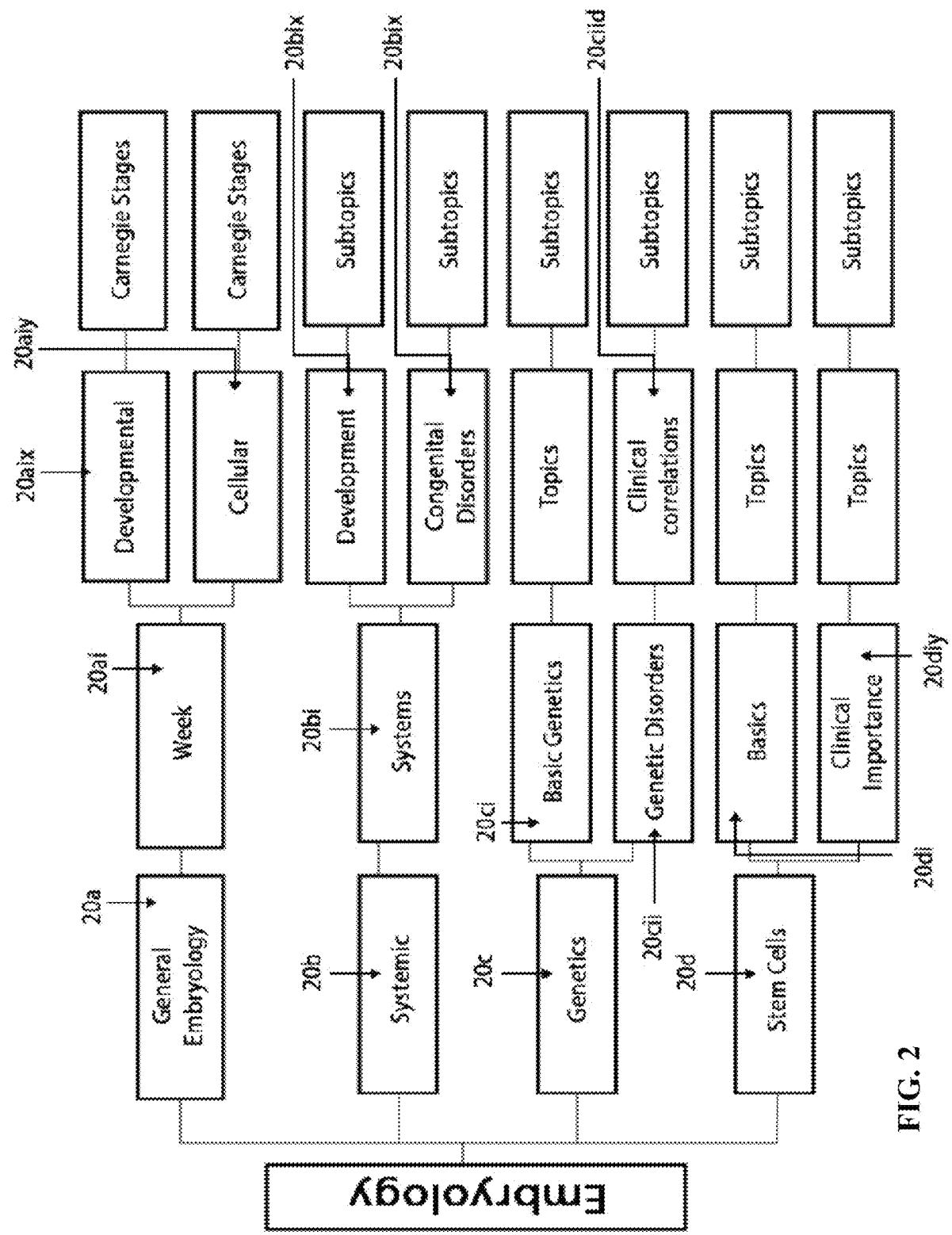
FIG. 2 illustrates a schematic representation of the sub-components of the interactive module (20) mainly for a general embryology module (20a), a systemic embryology module (20b), a genetics module (20c) and a stem cells module (20d)
Figure 3:
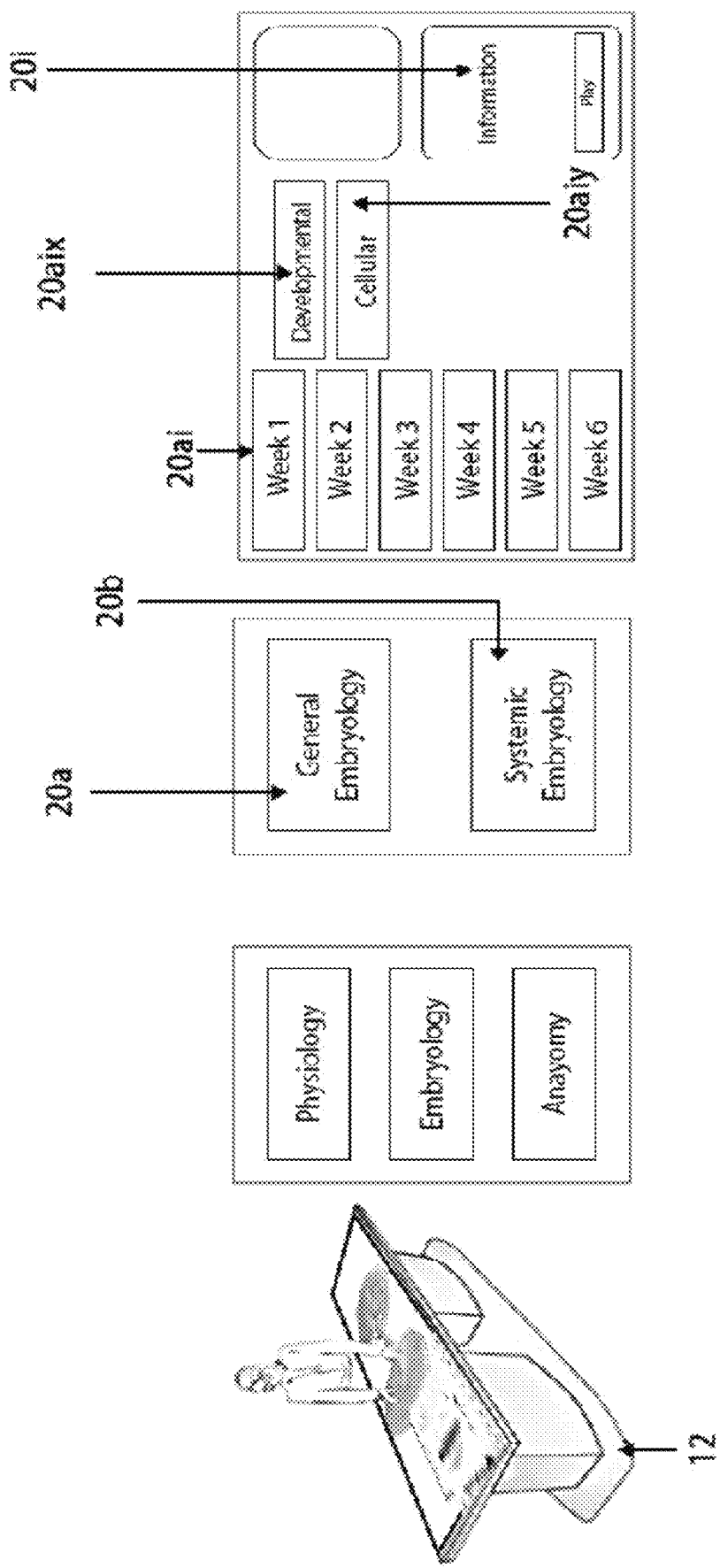
FIG. 3, FIG. 4, FIG. 5, FIG. 6, FIG. 7, FIG. 8, FIG. 9 and FIG. 10 illustrate schematic representations of weekly a development of developmental—carnegie stages module (20aix) and a cellular—carnegie stages module (20aiy) of the general embryology module (20a).
Figure 3:
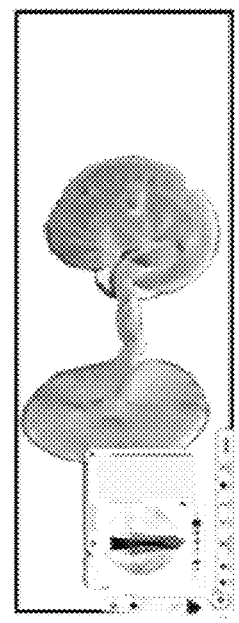
Figure 3:
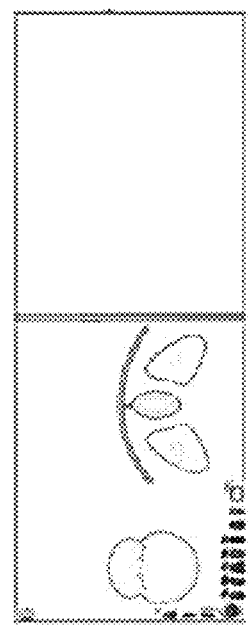
Figure 4:
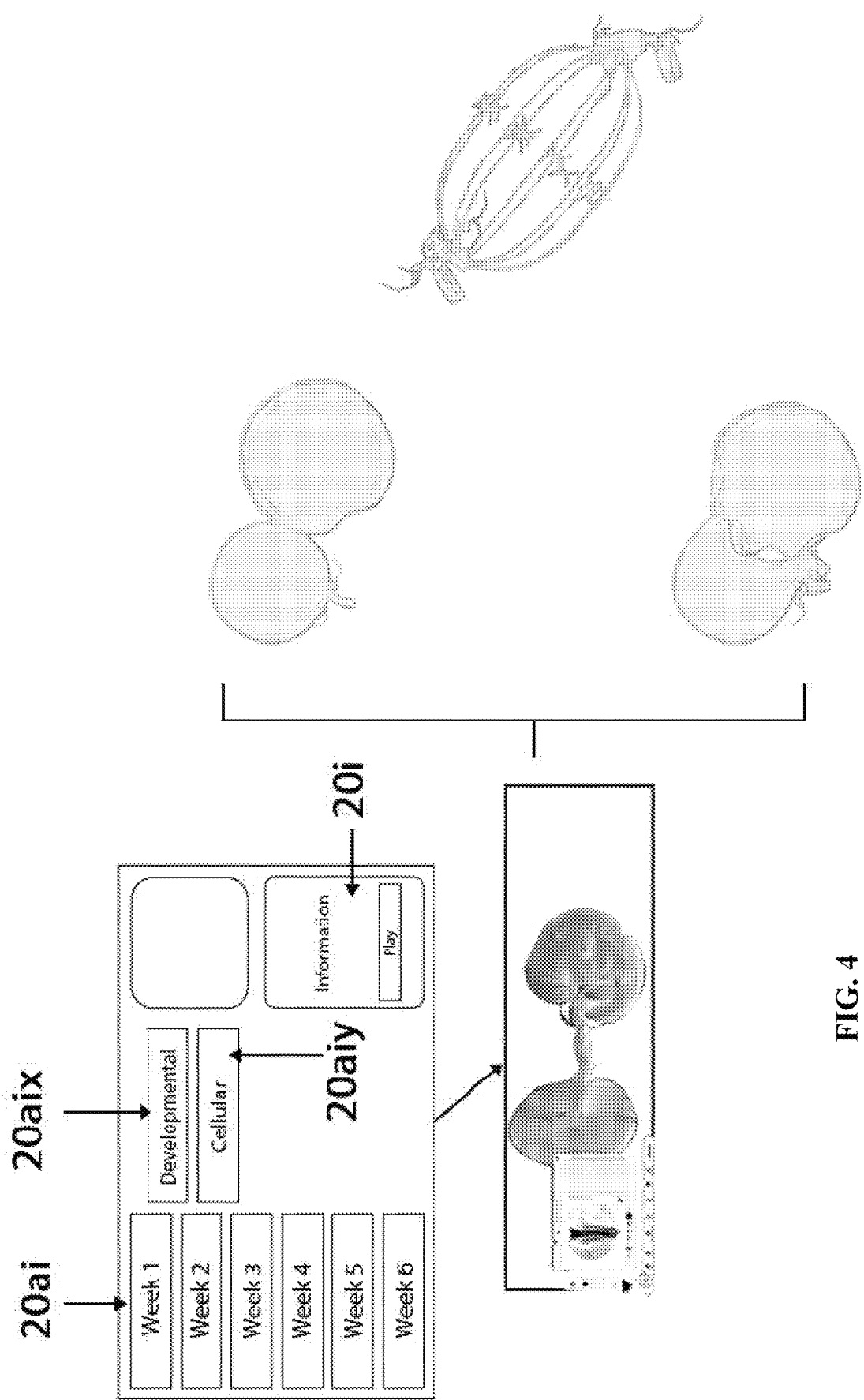
Figure 5:
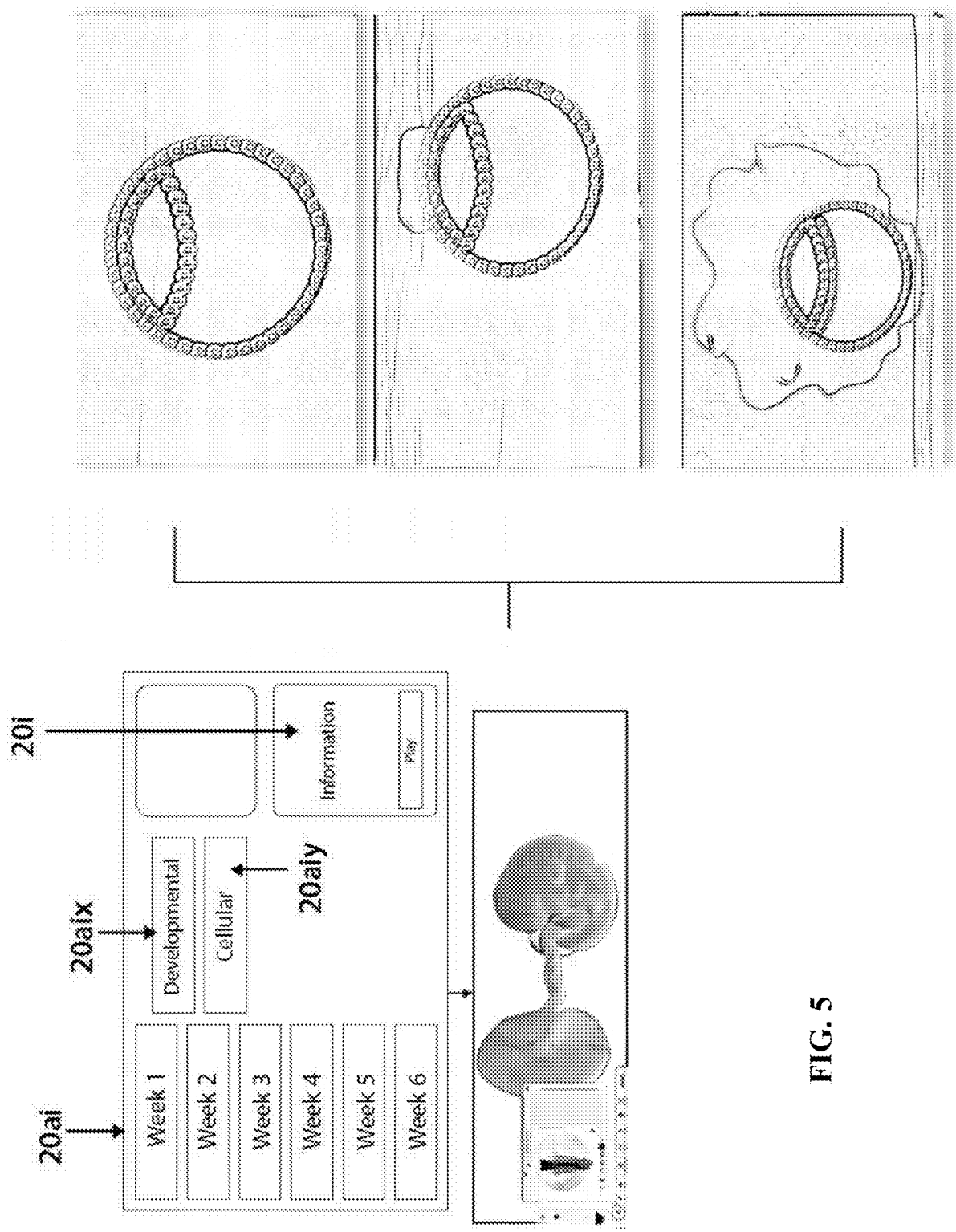
Figure 6:
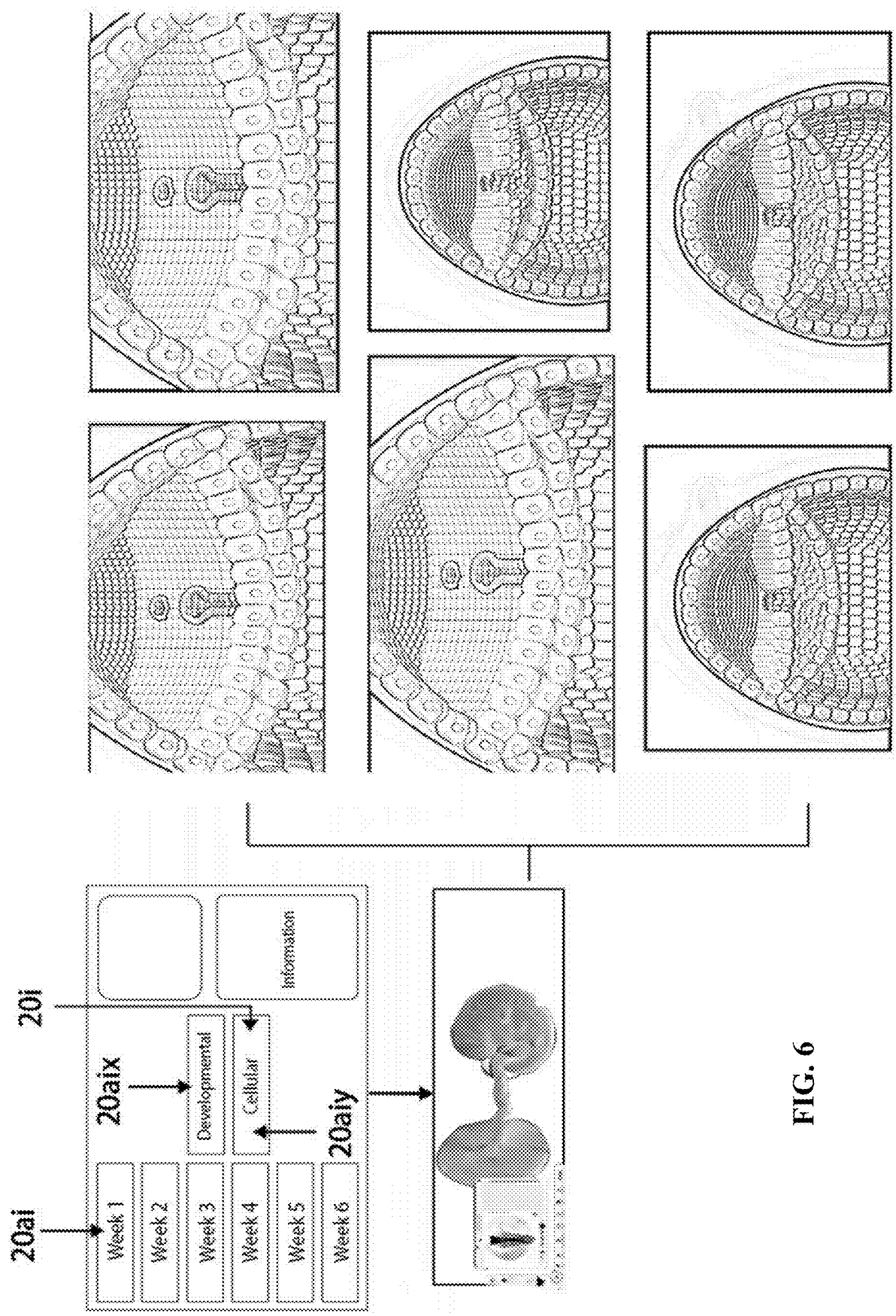
Figure 7:
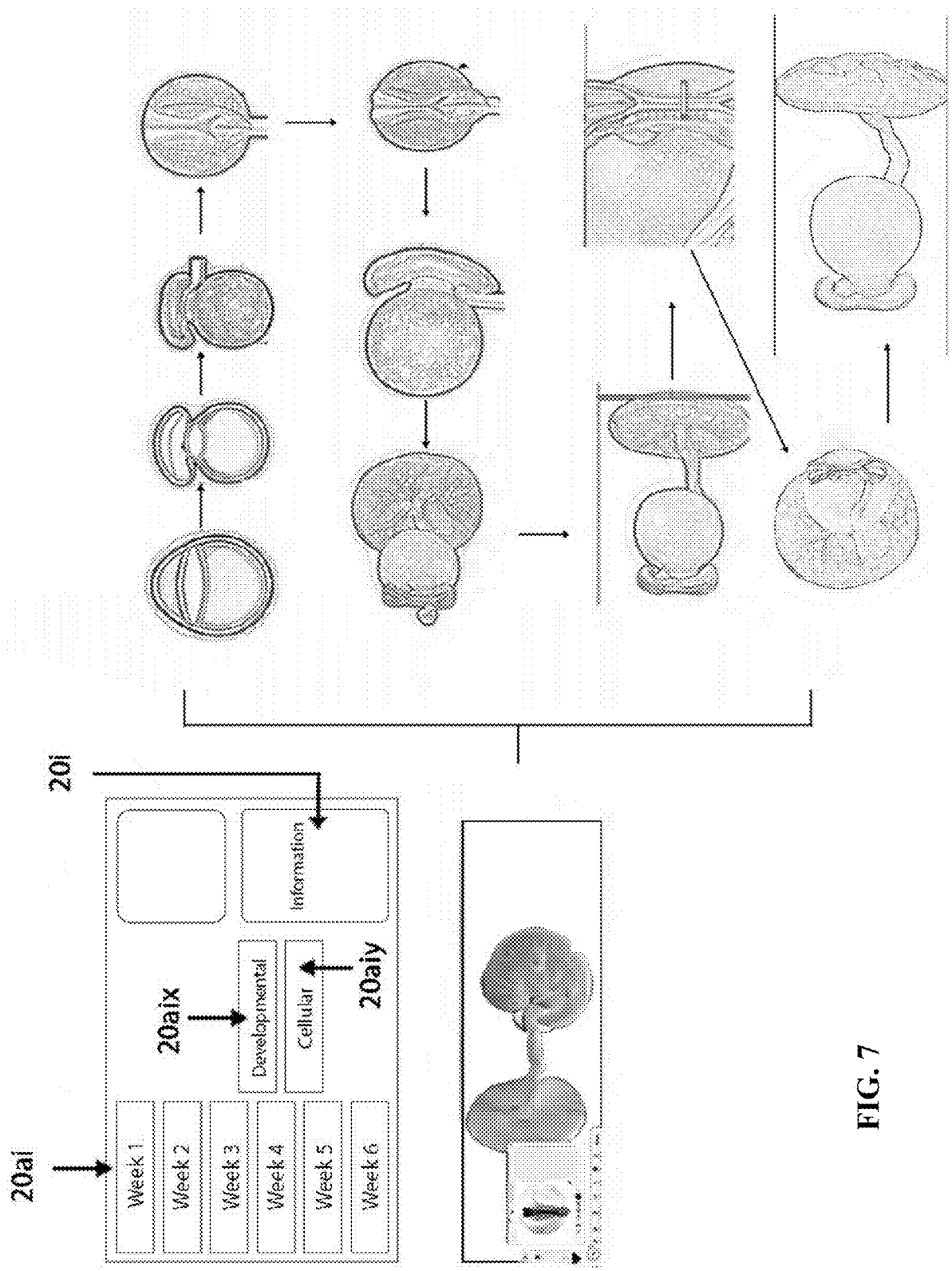
Figure 8:
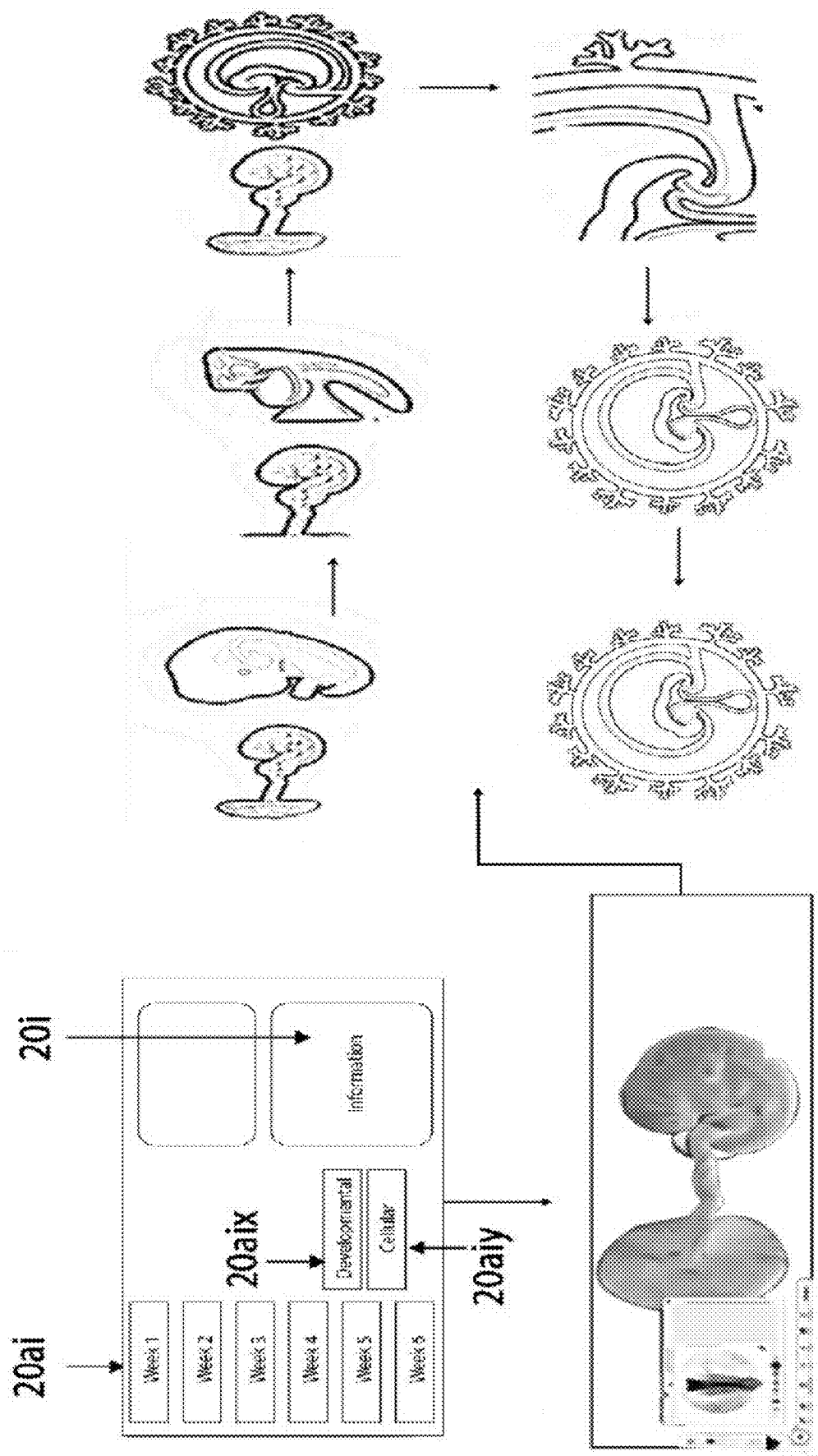
Figure 9:
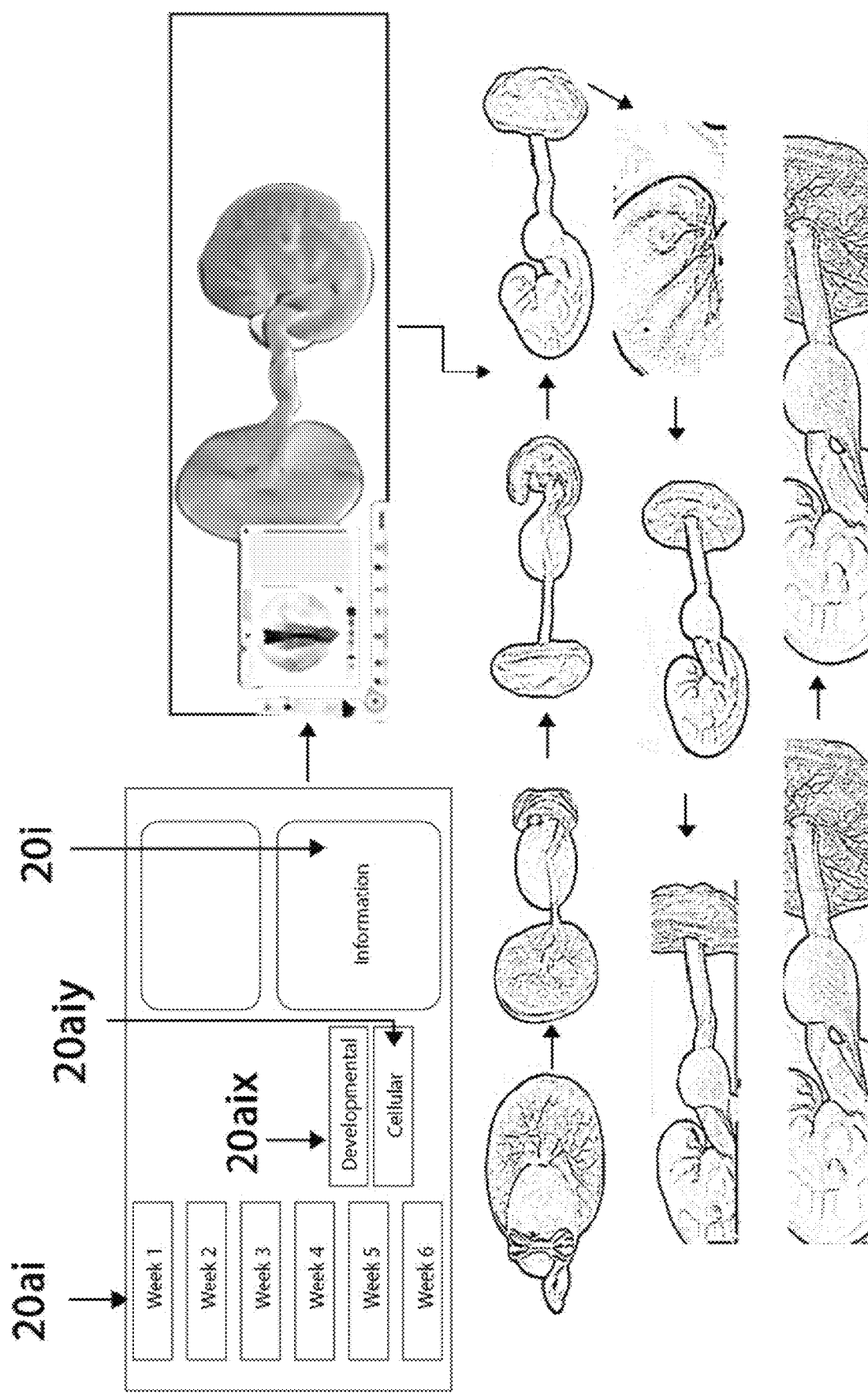
Figure 10:
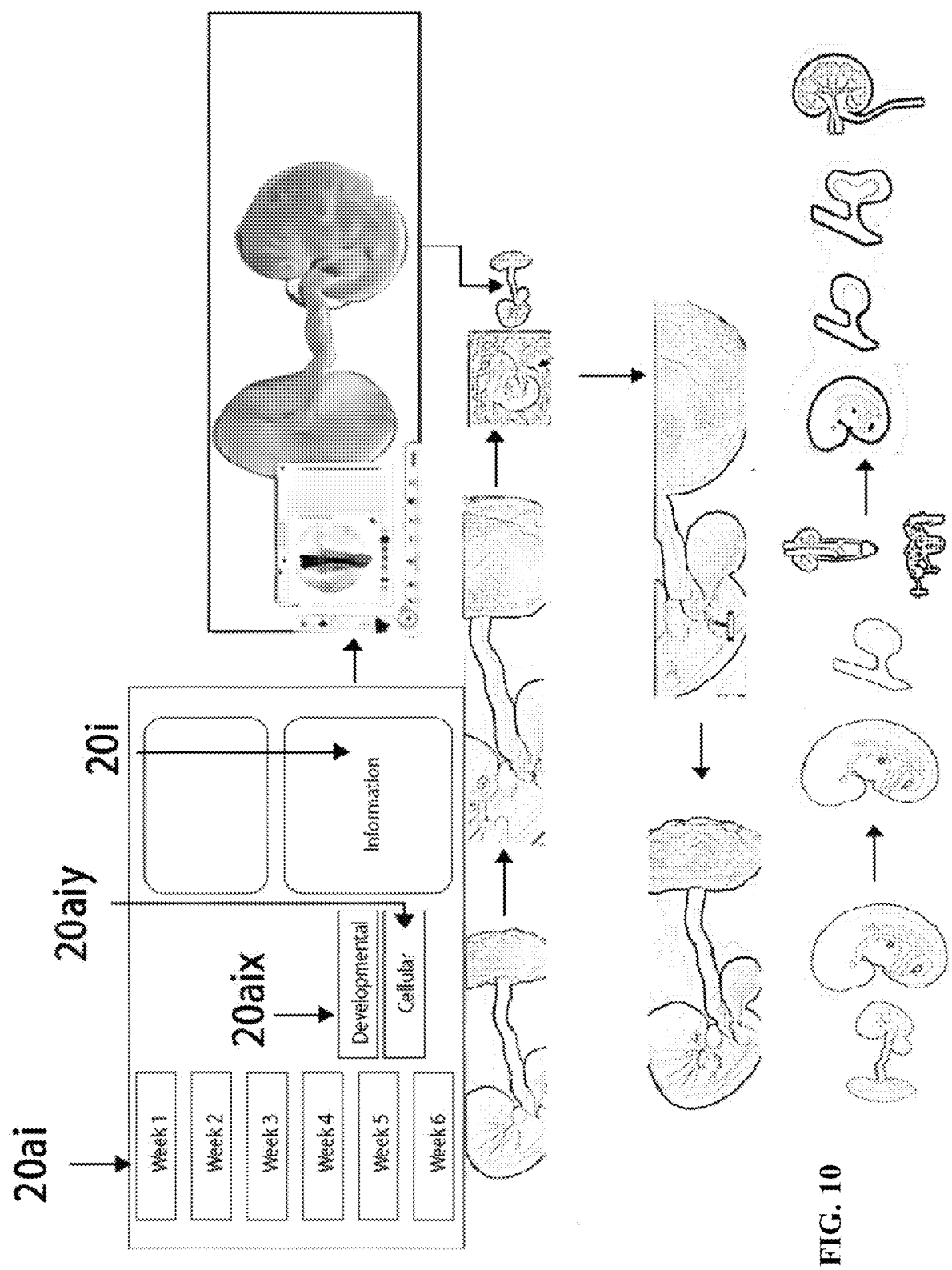

Referring now to the drawings, FIGS. 1 to 18, where the present invention is generally referred to with numeral (100), it can be observed that a system for simulation and understanding embryology system, in accordance with an embodiment, is provided which includes a processing system (10), an interactive module (20), a text module (30), an audio-video module (40) and a three-dimensional simulation module (50).

The processing system (10) is hosted on a server (11) and accessed through a device (12). The processing system (10) includes a registration module (not shown) to register one or more users by creating corresponding one or more user profiles. In one embodiment, the one or more users registered with the registration module via one or more user devices (12). The one or more user devices (12) may communicate with the processing system (10) via an application programming interface. The device (12) can be any network connected device such as 3-D interactive bed, smart phones, mobile phones, tablets, laptops, personal assistant devices, computers or the like. The device (12) mainly is required which facilitates 3-D interaction.

The interactive module (20) is the main module that receives a selection from a user of the four main embryology modules which includes a general embryology module (20a), a systemic embryology module (20b), a genetics module (20c) and a stem cells module (20d) and upon selection the display of the device (12) displays selected contents or sub-contents.

The general embryology module (20a) allows selection of a week module (20ai) that further allows selection from a developmental—carnegie stages module (20aix) and a cellular—carnegie stages module (20aiy). FIGS. 3 to 10 illustrates the some of the week module selection for both development—carnegie stages module (20aix) and a cellular—carnegie stages module (20aiy). Thus, a complete detailed understanding with 3-D view and 2-D views with further selection for information (20i) can be viewed.

Figure 11:
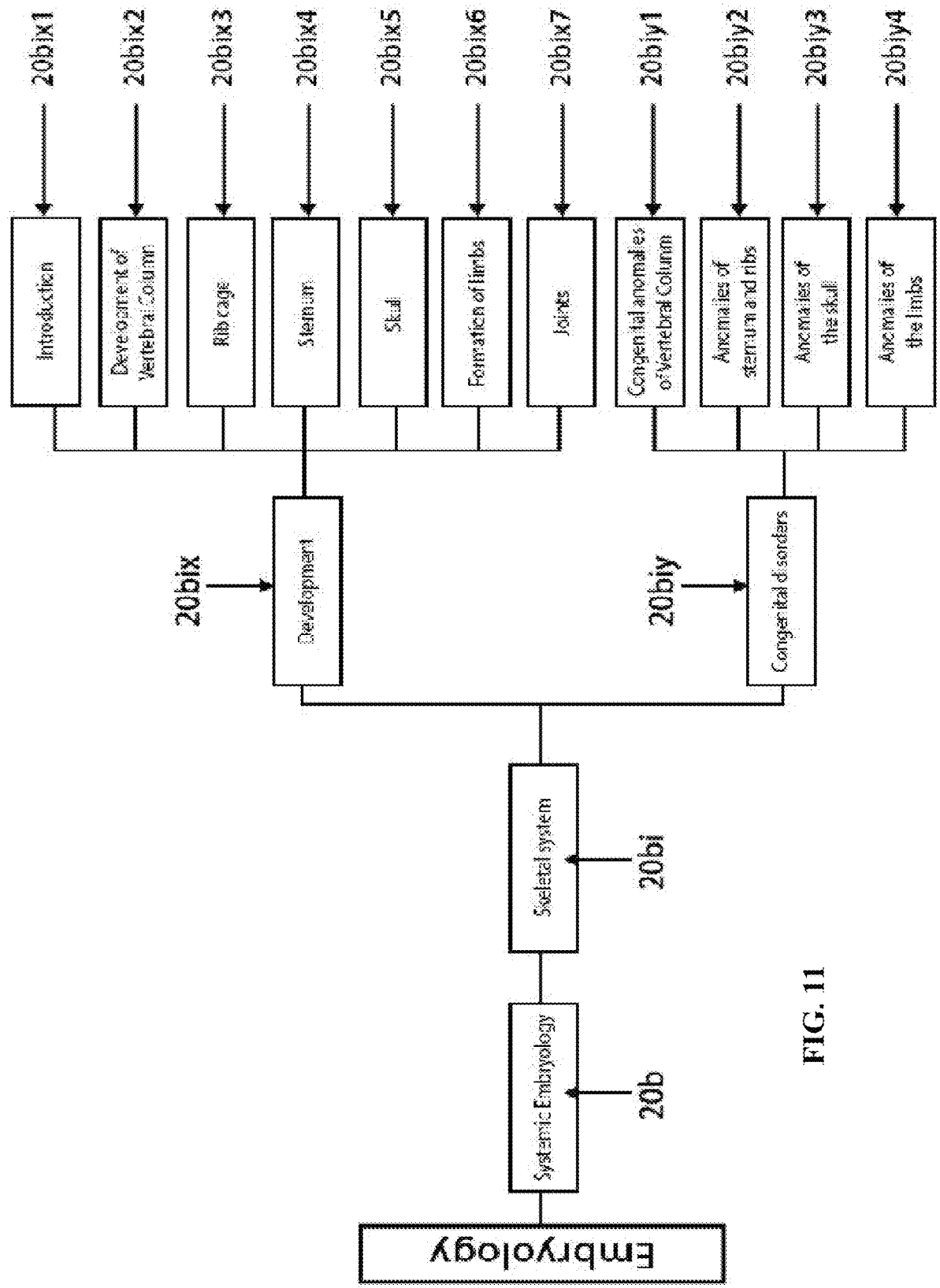
FIG. 11 illustrates schematic sub-representation of the systemic embryology module (20b)
Figure 12:
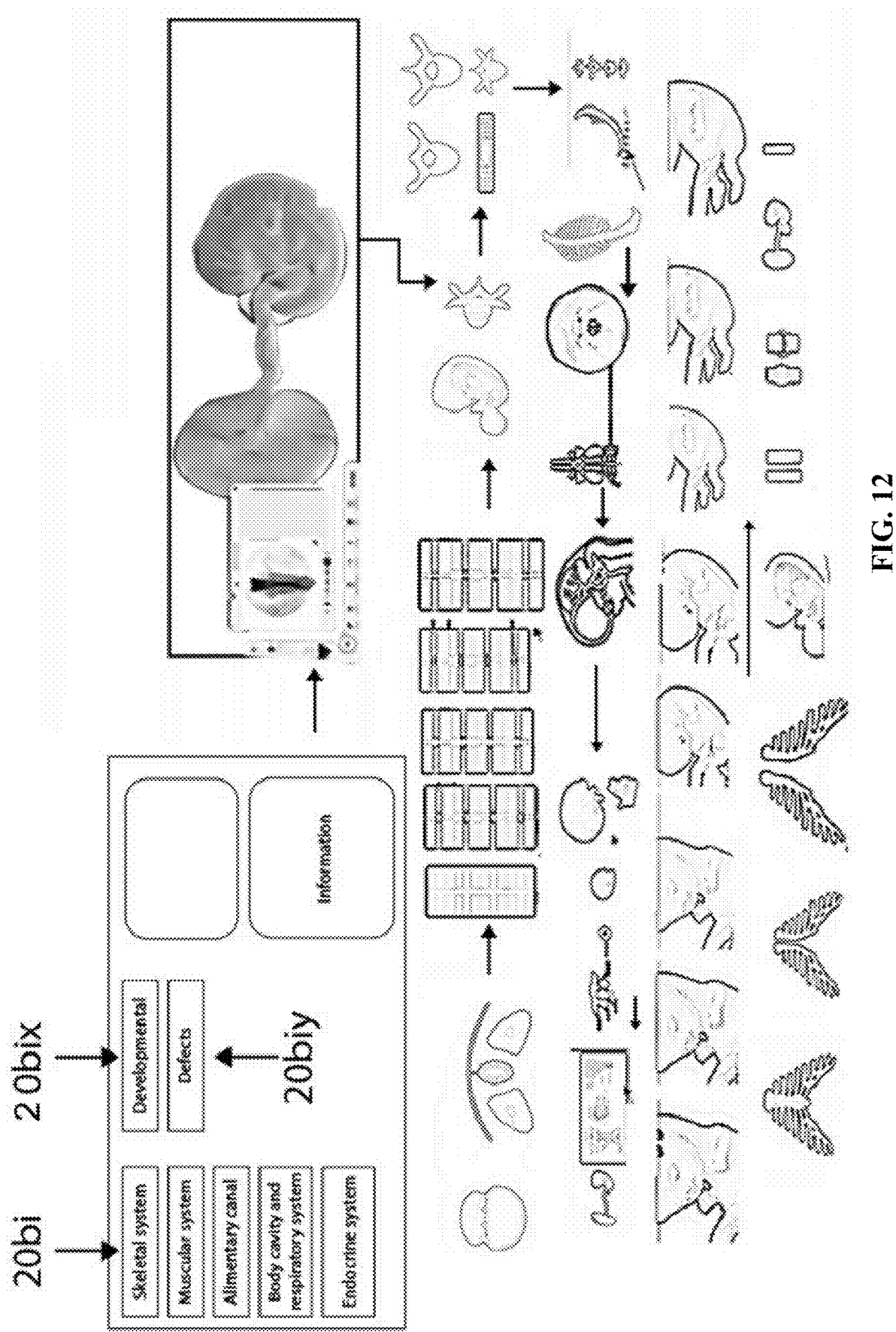
FIG. 12 illustrates a schematic sub-representation of the skeletal system module (20bi) of the systemic embryology module (20b)

The systemic embryology module (20b) allows selection of a skeletal system module (20bi) that further allows selection from a development module (20bix) and a congenital disorder module (20biy). The selection of the development module (20bix) allows selection from an introduction module (20bix1), a development of vertebral column module (20bix2), a rib cage module (20bix3), a sternum module (20bix4), a skull module (20bix5), a formation of limbs module (20bix6) and a joint module (20bix7). The selection of the congenital disorder module (20biy) allows selection from a congenital anomalies of vertebral column module (20biy1), an anomalies of sternum and ribs module (20biy2), an anomalies of the skull module (20biy3) and an anomalies of limbs module (20biy4). FIGS. 11 to 12 represent the systemic embryology module (20b).

Figure 13:
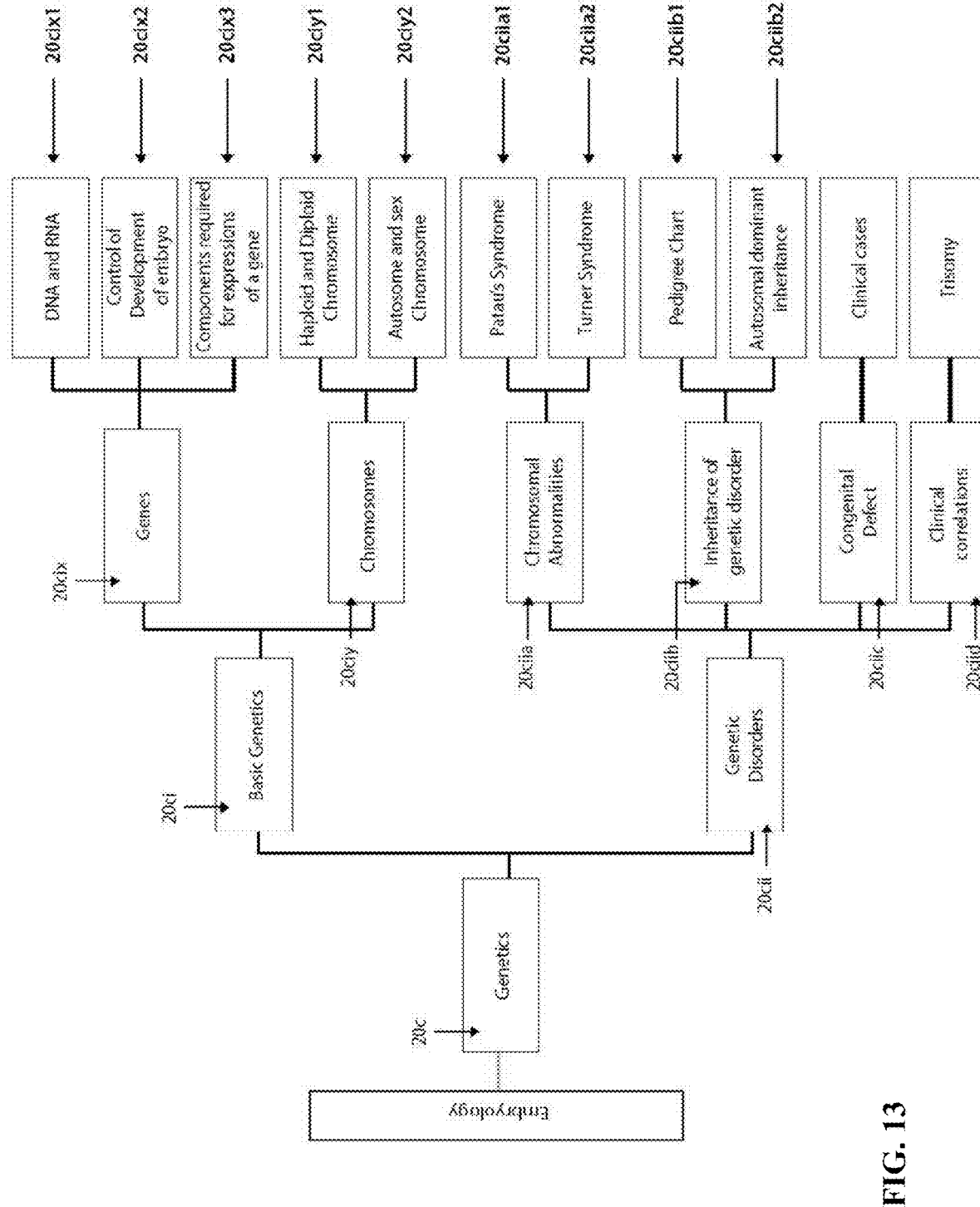
FIG. 13 illustrates a schematic sub-representation of the genetics module (20c)
Figure 14:
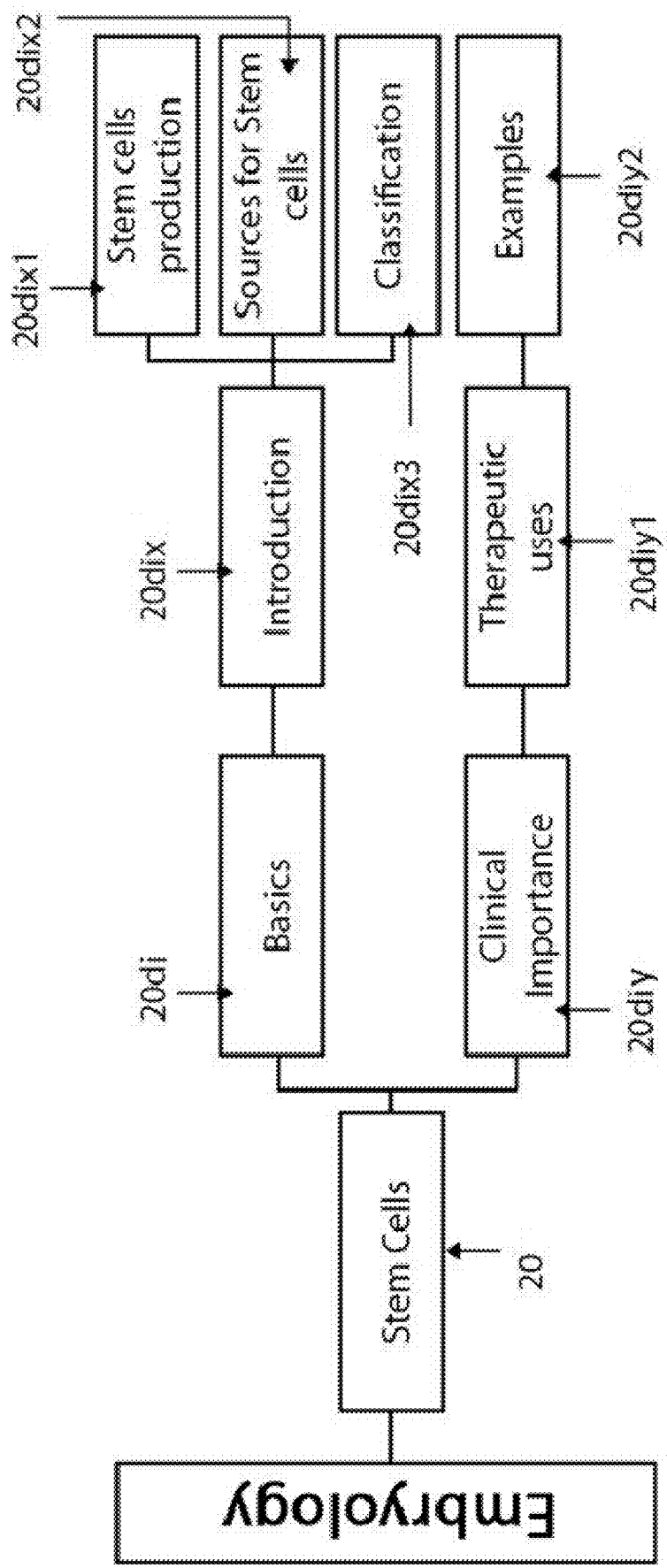
FIG. 14 illustrates a schematic sub-representation of the stem cells module (20d)
Figure 15:
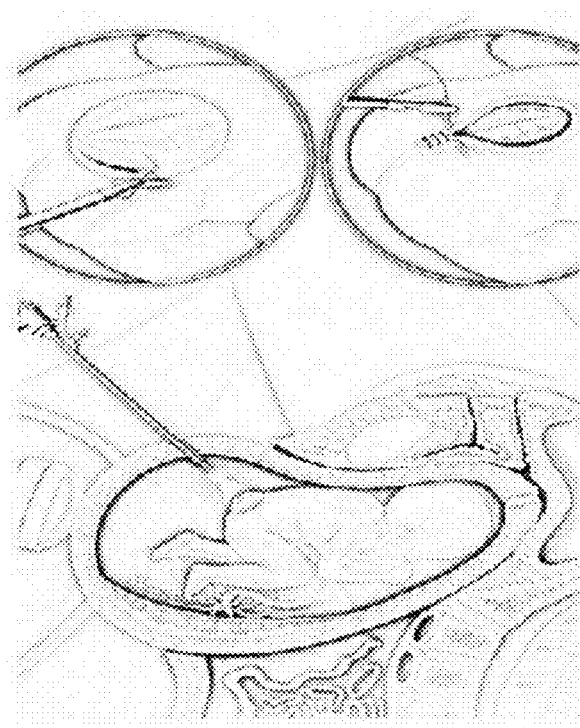
FIG. 15 illustrates a schematic sub-representation of a fetal surgery and intervention simulation module (60)
Figure 15:
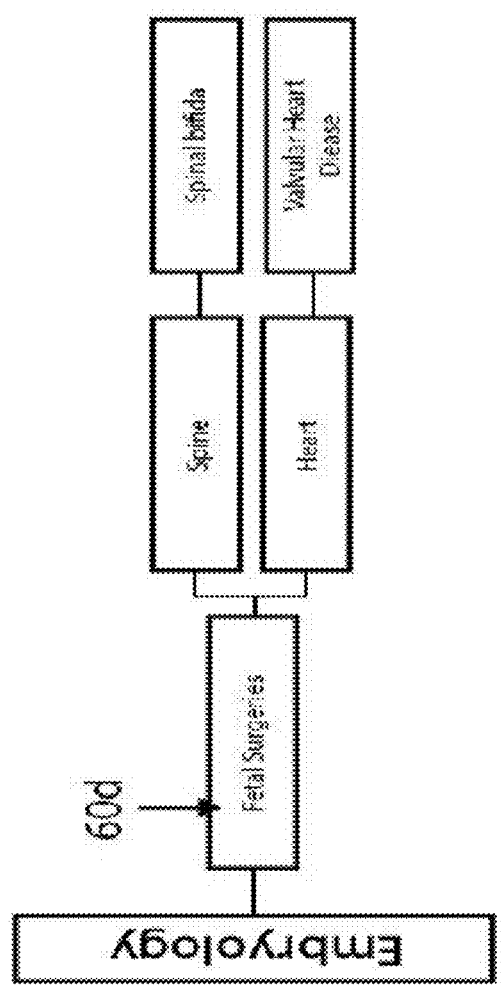
Figure 16:
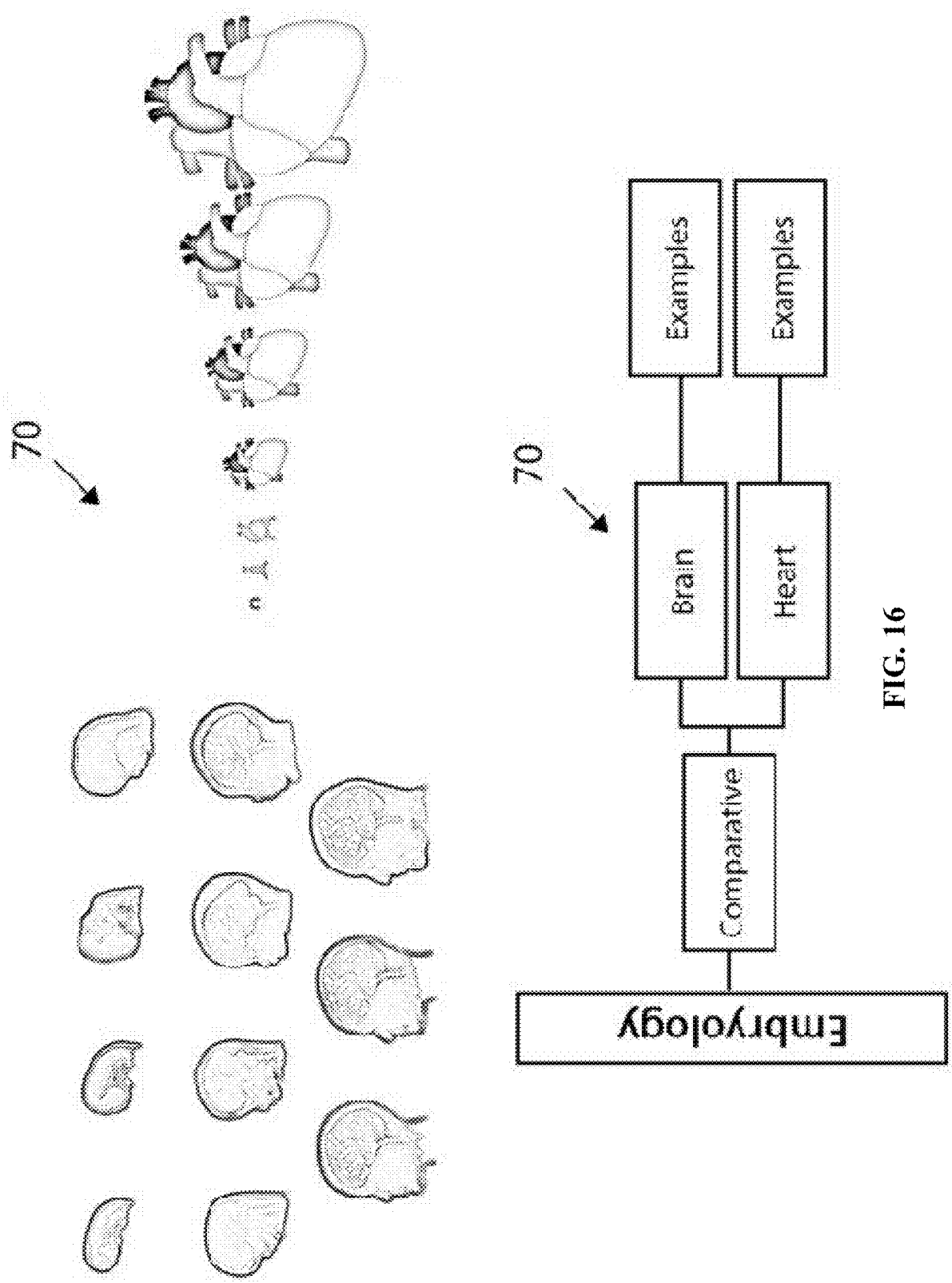
FIG. 16 illustrates a schematic sub-representation of a comparative module (70)

The genetics module (20c) allows selection for the basic genetic module (20ci) that further allows selections from a genes module (20cix) and a chromosomes modules (20ciy). The selection of the genes module (20cix) allows selection from: a DNA and RNA module (20cix1), a control of development of embryo module (20cix2), and a components required for expression of gene module (20cix3). The selection of the chromosomes module (20ciy) allows selection from a haploid module (20ciy1) and a diploid and chromosomes module (20ciy2). The selection of the genetic disorder module (20cii) allows selection from: a chromosomal abnormalities module (20ciia), an inheritance of genetic disorder module (20ciib), a congenital defect module (20ciic) and a clinical correlations module (20ciid). The selection of the chromosomal abnormalities module (20ciia) allows selection from a patau's syndrome module (20ciia1) and a turner syndrome module (20ciia2). The selection of the inheritance of genetic disorder module (20ciib) allows selection from a pedigree chart module (20ciib1) and an autosomal dominant inheritance module (20ciib2). FIG. 13 shows the representation of genetics module (20c).

The stem cells module (20d) allows selection of: a basic module (20di). The basic module (20di) allows selection of an introduction module (20dix) and a clinical importance module (20diy). The introduction module (20dix) allows selection of a stem cells production module (20dix1), a sources for stem cells module (20dix2) and a classification module (20dix3). The selection of the clinical importance module (20diy) allows selection from a therapeutic uses module (20diy1) and an example module (20diy2).

The text module (30) displays text from the selection of the interactive module (20). Moreover, the text module (30) displays text that explains the selected content. The text of the text module (30) is provided with links that can play the audio-video module (40), the three-dimensional simulation module (50), the fetal surgery and intervention simulation module (60) and the comparative module (70) and hence are interlinked.

The audio-video module (40) to play from the selection of the interactive module (20). The audio-video module (40) is provided with links that can display/play text of the text module (30), the three-dimensional simulation module (50), the fetal surgery and intervention simulation module (60) and the comparative module (70) and hence are interlinked.

The three-dimensional simulation module (50) allows simulation from the selection of the interactive module (20). The three-dimensional simulation module (50) is provided with links that can display/play text of the text module (30), the audio-video module (40), the fetal surgery and intervention simulation module (60) and the comparative module (70) and hence are interlinked.

The fetal surgery and intervention simulation module (60) enables to perform surgery through the three-dimensional simulation module (50). The fetal surgery and intervention simulation module (60) is provided with links that can display/play text of the text module (30), the audio-video module (40), the three-dimensional simulation module (50) and the comparative module (70) and hence are interlinked. The fetal surgery and intervention simulation module (60) provides procedure or steps to understand the step required to perform surgery. The simulation is performed by use of an oculus wearable on user's head and haptic sensors wearable in hands, wherein the oculus and haptic sensors are connected to the device (12). In another embodiment, the simulation is performed by operating the touch screen of the device (12).

The comparative module (70) allows comparison of fetal anatomical structures and physiology at different developmental stages of age to adults. The comparative module (70) is provided with links that can display/play text of the text module (30), the audio-video module (40), the three-dimensional simulation module (50) and the fetal surgery and intervention simulation module (60) and hence are interlinked.

Figure 17:
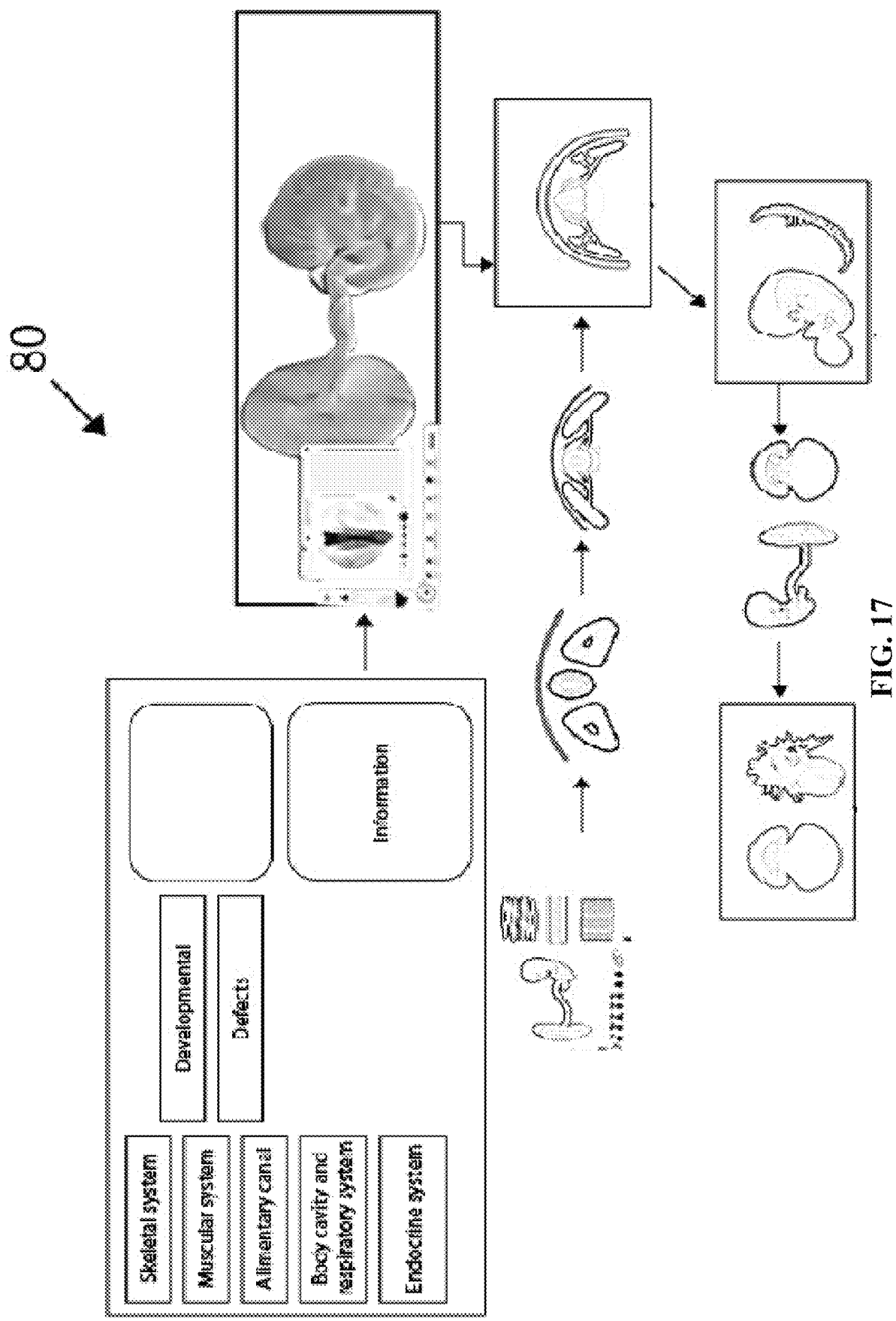
FIG. 17 illustrates a schematic sub-representation of a muscular system module (80)
Figure 18:
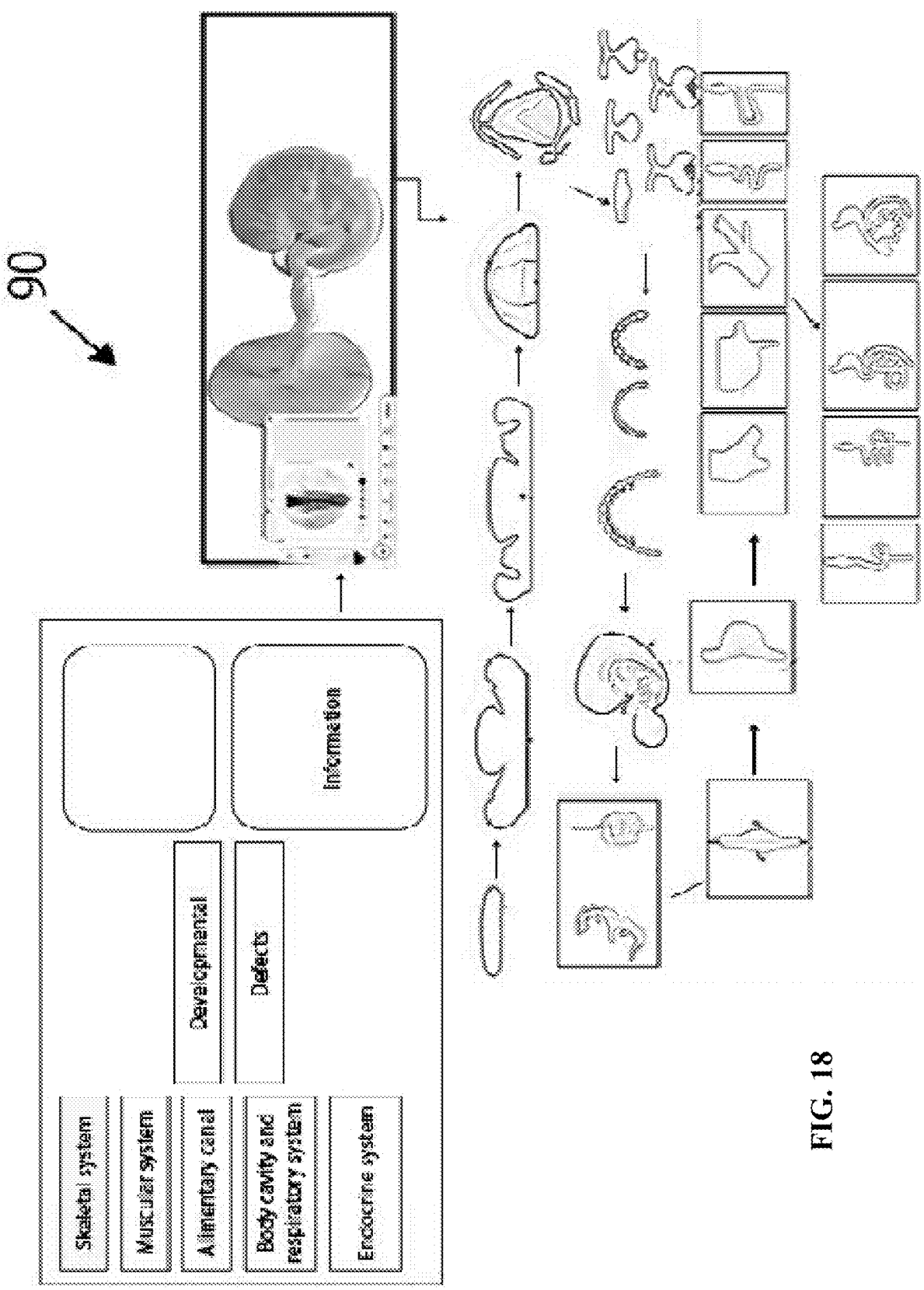
FIG. 18 illustrates a schematic sub-representation of an alimentary canal module (90).

Additionally, the present disclosure includes a muscular system module, an alimentary canal module, a body cavity and respiratory system module and an endocrine system. The muscular system module (80) is illustrated in FIG. 17. The alimentary canal module (90) is illustrated in FIG. 18.

The present disclosure also discloses a method for simulation and understanding embryology. The best-method includes providing the simulation and understanding embryology system (100) defined with the processing system (10), the interactive module (20), the text module (30), the audio-video module (40) and the three-dimensional simulation module (50), the fetal surgery and intervention simulation module (60) and the comparative module (70).

The method includes selecting, by a user from the interactive module (20), the general embryology module (20a), the systemic embryology module (20b), the genetics module (20c) and the stem cells module (20d).

The selection of the general embryology module (20a) allows selection of the week module (20ai) that further allows selection from a developmental—carnegie stages module (20aix) and a cellular—carnegie stages module (20aiy).

The selection of the systemic embryology module (20b) allows selection of a skeletal system module (20bi) that further allows selection from the development module (20bix) and the congenital disorder module (20biy). The selection of the development module (20bix) allows selection from the introduction module (20bix1), the development of vertebral column module (20bix2), the rib cage module (20bix3), the sternum module (20bix4), the skull module (20bix5), the formation of limbs module (20bix6) and the joints module (20bix7). The selection of the congenital disorder module (20biy) allows selection from the congenital anomalies of vertebral column module (20biy1), the anomalies of sternum and ribs module (20biy2), the anomalies of the skull module (20biy3) and the anomalies of limbs module (20biy4).

The selection of the genetics module (20c) allows selection for the basic genetic module (20ci) that further allows selections from the genes module (20cix) and the chromosomes modules (20ciy). The selection of the genes module (20cix) allows selection from: the DNA and RNA module (20cix1), the control of development of embryo module (20cix2), and the components required for expression of gene module (20cix3). The selection of the chromosomes module (20ciy) allows selection from the haploid module (20ciy1) and the diploid and chromosomes module (20ciy2). The selection of the genetic disorder module (20cii) allows selection from: the chromosomal abnormalities module (20ciia), the inheritance of genetic disorder module (20ciib), the congenital defect module (20ciic) and the clinical correlations module (20ciid). The selection of the chromosomal abnormalities module (20ciia) allows selection from the patau's syndrome module (20ciia1) and the turner syndrome module (20ciia1). The selection of the inheritance of genetic disorder module (20ciib) allows selection from the pedigree chart module (20ciib1) and the autosomal dominant inheritance module (20ciib2).

The selection of the stem cells module (20d) allows selection of: the basic module (20di) to allow selection of the introduction module (20dix) and the clinical importance module (20diy), the introduction module (20dix) allows selection of a stem cells production module (20dix1), the sources for stem cells module (20dix2) and the classification module (20dix3). The selection of the clinical importance module (20diy) allows selection from the therapeutic uses module (20diy1) and the example module (20diy2).

The selecting, by the user through the device (12), the text module (30) to display text from the selection of the interactive module (20). The selecting, by the user through the device (12), the audio-video module (40) to play from the selection of the interactive module (20). The method includes selecting, by the user through the device (12), the three-dimensional simulation module (50) to allow simulation from the selection of the interactive module (20). The method includes performing, by the user through the device (12), three-dimensional simulation by the user through the device (12). The method includes conducting surgery in the fetal surgery and intervention simulation module (60). The method includes conducting comparison, in the comparative module (70), of fetal anatomical structures and physiology at different developmental stages of age to adults. To perform the method the interactive module (20), the text module (30), the audio-video module (40), the three-dimensional simulation module (50), the fetal surgery and intervention simulation module (60) and the comparative module are interlinked.

Typically, the method includes performing the simulation by use of the oculus wearable on user's head and haptic sensors wearable in hands. In which the oculus and haptic sensors are connected to the device (12). Alternatively, the method includes performing simulation by operating the touch screen of the device (12).

The foregoing description conveys the best understanding of the objectives and advantages of the present invention. Different embodiments, steps or alternatives may be made of the inventive concept of this invention. It is to be understood that all matter disclosed herein is to be interpreted merely as illustrative, and not in a limiting sense.

What is claimed is:

1. A simulation system for embryology comprising:
   a processing system hosted on a server and accessible by a registered device, wherein said processing system comprising:
   an interactive module including the following selectable options:
   (1) a general embryology module, (2) a systemic embryology module, (3) a genetics module, and (4) a stem cells module, (1) said general embryology module includes a week module,
    wherein said week module includes selectable options: a developmental—camogie stages module and a cellular—carnegie stages module;
(2) said systemic embryology module includes of a skeletal system module, wherein said skeletal system module includes selectable options: a development module and a congenital disorder module,
    wherein said development module includes selectable options: an introduction module, a development of vertebral column module, a rib cage module, a sternum module, a skull module, a formation of limbs module and joints module,
    wherein said congenital disorder module includes selectable options: a congenital anomalies of vertebral column module, an anomalies of sternum and ribs module, an anomalies of the skull module and an anomalies of limbs module;
(3) said genetics module includes a basic genetic module and a genetic disorders module,
    wherein said genetic module includes selectable options: a genes module and a chromosomes modules,
        wherein said genes module includes selectable options: a DNA and RNA module, a control of development of embryo module, and a components required, for expression of gene module,
        wherein said chromosomes module includes selectable options: a haploid module and a diploid module, and autosome and sex chromosomes module,
    wherein said genetic disorder module includes selectable options: a chromosomal abnormalities module, an inheritance of genetic disorder module, a congenital defect module and a clinical correlations module;
        wherein said chromosomal abnormalities module includes selectable options: a patau's syndrome module and a turner syndrome module,
        wherein said inheritance of genetic disorder module includes selectable options: a pedigree chart module and an autosomal dominant inheritance module;
(4) said stem cells module includes selectable options: a basic module and a clinical important module,
    wherein said basic module includes an introduction module,
        wherein said introduction module includes selectable options: a stem cells production module, a sources for stem cells module and a classification module,
    wherein said clinical importance module includes a therapeutic uses module,
        wherein said therapeutic uses module includes an example module;
        a text module configured to display text from the selection of said interactive module;
        an audio-video module configured to play the audio and video content from the selection of said interactive module;
        a three-dimensional simulation module configured to allow simulation from the selection of said interactive module;
        a fetal surgery and intervention simulation module to configure to provide simulated surgery through said three-dimensional simulation module; and
        a comparative module configured to compare fetal anatomical structures and physiology at different developmental stages of age to adults;
            wherein said interactive module, said text module, said audio-video module, said three-dimensional simulation module, said fetal surgery and intervention simulation module and said comparative module are interlinked.

2. The simulation system for embryology system as claimed in claim 1, wherein said simulation adapted by a virtual reality headset and haptic sensors handheld device, wherein said virtual reality headset and said haptic sensors handheld device are connected to said registered device.

3. The simulation system for embryology system as claimed in claim 1, wherein said simulation is performed by operating the touch screen of said device.

4. A simulating method for embryology, comprising:
    providing a simulation and understanding embryology system includes a processing system, an interactive module, a text module, an audio-video module, a three-dimensional simulation module, a fetal surgery and intervention simulation module and a comparative module;
    selecting, by a user through a registered device, from said interactive module, wherein selectable options include:
        (1) a general embryology module, (2) a systemic embryology module, (3) a genetics module and (4) a stem cells module,
    (1) said general embryology module includes a week module wherein said week module includes selectable options: a developmental—camogie stages module and a cellular—carnegie stages module;
    (2) said systemic embryology module includes of a skeletal system module, wherein said skeletal system module includes selectable options: a development module and a congenital disorder module,
        wherein said development module includes selectable options: an introduction module, a development of vertebral column module, a rib cage module, a sternum module, a skull module, a formation of limbs module and joints module,
        wherein said congenital disorder module includes selectable options: a congenital anomalies of vertebral column module, an anomalies of sternum and ribs module, an anomalies of the skull module and an anomalies of limbs module;
    (3) said genetics module includes a basic genetic module and a genetic disorders module,
    wherein said genetic module includes selectable options: a genes module and a chromosomes modules,
        wherein said genes module includes selectable options: a DNA and RNA module, a control of development of embryo module, and a components required for expression of gene module,
        wherein said chromosomes module includes selectable options: a haploid module and a diploid module and autosome and sex chromosomes module,
    wherein said genetic disorder module includes selectable options: a chromosomal abnormalities module, an inheritance of genetic disorder module, a congenital defect module and a clinical correlations module;

wherein said chromosomal abnormalities module includes selectable options: a patau's syndrome module and a turner syndrome module,
wherein said inheritance of genetic disorder module includes selectable options: a pedigree chart module and an autosomal dominant inheritance module;
(4) said stem cells module includes selectable options: a basic module and a clinical important module,
wherein said basic module includes an introduction module,
wherein said introduction module includes selectable options: a stem cells production module, a sources for stem cells module and a classification module,
wherein said clinical importance module includes a therapeutic uses module
wherein said therapeutic uses module includes an example module;
displaying textual data, through a textual module, based on the selections in said interactive module;
playing audio and video content, through the audio-video module, based on the selections of said interactive module;
selecting, by the user through said registered device, a three-dimensional simulation module to allow simulation from the selections of said interactive module;
performing, by the user through said registered device, three-dimensional simulation by the user;
conducting surgery in a fetal surgery and intervention simulation module; and
conducting comparison, through a comparative module, of fetal anatomical structures and physiology at different developmental stages of age to adults;
wherein said interactive module, said text module, said audio-video module, said three-dimensional simulation module, said fetal surgery and intervention simulation module and said comparative module are interlinked.

5. The simulating method for embryology as claimed in claim 4, wherein said simulation adapted by a virtual reality headset and haptic sensors handheld device, wherein said virtual reality headset and said haptic sensors handheld device are connected to said registered device.

6. The simulating method for embryology as claimed in claim 4, wherein said simulation adapted by a touch screen of said registered device.

\* \* \* \* \*